US00PP17458P2

(12) United States Plant Patent
van der Helm

(10) Patent No.: US PP17,458 P2
(45) Date of Patent: Feb. 27, 2007

(54) ***ANTIRRHINUM* PLANT NAMED 'AMALIA PINK'**

(50) Latin Name: *Antirrhinum majus*
Varietal Denomination: Amalia Pink

(75) Inventor: Franciscus Jacobus Joseph van der Helm, Aalsmeer (NL)

(73) Assignee: P. Kooij + Zonen B.V., Aalsmeer (NL)

( * ) Notice: Subject to any disclaimer, the term of this patent is extended or adjusted under 35 U.S.C. 154(b) by 0 days.

(21) Appl. No.: 11/188,969

(22) Filed: Jul. 25, 2005

(51) Int. Cl.
*A01H 5/00* (2006.01)

(52) U.S. Cl. ..... Plt./322
(58) Field of Classification Search ..... Plt./322
See application file for complete search history.

*Primary Examiner*—Kent Bell
(74) *Attorney, Agent, or Firm*—C. A. Whealy

(57) ABSTRACT

A new and distinct cultivar of *Antirrhinum* plant named 'Amalia Pink', characterized by its upright and compact plant habit; freely branching habit; dense and bushy growth habit; dark green-colored leaves; freely flowering habit; and flowers that are dark pink in color.

1 Drawing Sheet

Botanical designation: *Antirrhinum majus.*
Cultivar denomination: 'Amalia Pink'.

BACKGROUND OF THE INVENTION

The present Invention relates to a new and distinct cultivar of *Antirrhinum* plant, commercially known as a pot-type Snapdragon, botanically known as *Antirrhinum majus,* and hereinafter referred to by the cultivar name Amalia Pink.

The new *Antirrhinum* is a product of a planned breeding program conducted by the Inventor in Aalsmeer, The Netherlands. The objective of the breeding program is to create new freely flowering *Antirrhinums* with upright and compact plant habit, and attractive flower coloration.

The new *Antirrhinum* originated from a cross-pollination made by the Inventor in Aalsmeer, The Netherlands, of an unnamed proprietary selection of *Antirrhinum majus,* not patented, as the female, or seed parent, with an unnamed proprietary selection of *Antirrhinum majus,* not patented, as the male, or pollen parent. The new *Antirrhinum* was discovered and selected as a single plant from the resulting progeny of the cross-pollination in a controlled environment in Aalsmeer, The Netherlands.

Asexual reproduction of the new cultivar by terminal vegetative cuttings since 2001, in Aalsmeer, The Netherlands has shown that the unique features of this new *Antirrhinum* are stable and reproduced true to type in successive generations.

SUMMARY OF THE INVENTION

Plants of the cultivar Amalia Pink have not been observed under all possible environmental conditions. The phenotype may vary somewhat with variations in environment such as temperature, light intensity and daylength without, however, any variance in genotype.

The following traits have been repeatedly observed and are determined to be the unique characteristics of 'Amalia Pink'. These characteristics in combination distinguish 'Amalia Pink' as a new and distinct cultivar:

1. Upright and compact plant habit.
2. Freely branching habit; dense and bushy growth habit.

3. Dark green-colored leaves.
4. Freely flowering habit.
5. Flowers that are dark pink in color.

Plants of the new *Antirrhinum* can be compared to plants of the female parent selection. In side-by-side comparisons conducted in Aalsmeer, The Netherlands, plants of the new *Antirrhinum* differed from plants of the female parent selection in the following characteristics:

1. Plants of the new *Antirrhinum* had smaller leaves than plants of the female parent selection.
2. Plants of the new *Antirrhinum* and the female parent selection differed in flower color.

Plants of the new *Antirrhinum* can be compared to plants of the male parent selection. In side-by-side comparisons conducted in Aalsmeer, The Netherlands, plants of the new *Antirrhinum* differed from plants of the male parent selection in the following characteristics:

1. Plants of the new *Antirrhinum* were more freely branching than plants of the male parent selection.
2. Plants of the new *Antirrhinum* and the male parent selection differed in flower color and shape.

Plants of the new *Antirrhinum* can be compared to plants of the cultivar Balumhopi, disclosed in U.S. Plant Pat. No. 13,628. In side-by-side comparisons conducted in Aalsmeer, The Netherlands, plants of the new *Antirrhinum* differed from plants of the cultivar Balumhopi in the following characteristics:

1. Plants of the new *Antirrhinum* were more compact and more upright than plants of the cultivar Balumhopi.
2. Plants of the new *Antirrhinum* had shorter internodes than plants of the cultivar Balumhopi.
3. Plants of the new *Antirrhinum* had smaller leaves than plants of the cultivar Balumhopi.
4. Plants of the new *Antirrhinum* and the cultivar Balumhopi differed in flower color.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new *Antirrhinum.* The photograph comprises a side perspective view of typical plants of 'Amalia Pink' grown in a container.

DETAILED BOTANICAL DESCRIPTION

Plants of the cultivar Amalia Pink have not been observed under all possible environmental conditions. The phenotype may vary somewhat with variations in environment such as temperature and light intensity, without, however, any variance in genotype.

The aforementioned photograph and following observations and measurements describe plants grown in Aalsmeer, The Netherlands, under commercial practice in a glass-covered greenhouse with day temperatures about 20° C., night temperatures about 12° C. and light levels about 10,000 lux. Plants used for the photographs and description were about three months from planting rooted cuttings in containers. In the following description, color references are made to The Royal Horticultural Society Colour Chart, 1995 Edition, except where general terms of ordinary dictionary significance are used.

Botanical classification: *Antirrhinum majus* cultivar Amalia Pink.

Parentage:

*Female parent.*—Unnamed proprietary selection of *Antirrhinum majus,* not patented.

*Male parent.*—Unnamed proprietary selection of *Antirrhinum majus,* not patented.

Propagation:

*Type cutting.*—Terminal vegetative cuttings.

*Time to initiate roots.*—Summer: About 5 days at 22° C. soil temperature. Winter: About 6 days at 22° C. soil temperature.

*Time to develop roots.*—Summer: About 14 days at 22° C. soil temperature. Winter: About 17days at 14° C. to 22° C. soil temperature.

*Root description.*—Fine; white in color.

*Rooting habit.*—Freely branching.

Plant description:

*Form.*—Annual flowering plant; upright and compact plant habit. Freely branching habit; dense and busy growth habit; about six lateral branches per plant.

*Plant height.*—About 12 cm.

*Plant diameter* (*area of spread*), *single plant.*—About 25 cm.

*Vigor.*—Rapid growth rate; vigorous.

*Lateral branches.*—Length: About 10 cm. Diameter: About 4 mm. Internode length: About 5 mm. Texture: Smooth, glabrous. Color: 144B.

*Foliage description.*—Arrangement: Alternate, simple. Length: About 3.5 cm. Width: About 1 cm. Shape: Elliptic. Apex: Rounded to broadly acute. Base: Attenuate. Margin: Entire. Texture, upper and lower surfaces: Smooth, glabrous. Venation pattern: Pinnate, arcuate. Color: Developing leaves, upper surface: 137A. Developing leaves, lower surface: 137C. Fully expanded leaves, upper surface: 139A. Fully expanded leaves, lower surface: 137B. Venation, upper and lower surfaces: Similar to lamina. Petiole length: About 1 cm. Petiole diameter: About 2 mm. Petiole texture, upper and lower surfaces: Smooth, glabrous. Petiole color, upper and lower surfaces: 137C.

Flower description:

*Flower type and habit.*—Single bi-labiate flowers arranged in terminal racemes. Freely flowering habit, usually about eight flowers per raceme. Flowers face mostly outwardly. Flowers not persistent. Flowers fragrant.

*Natural flowering season.*—Long flowering period throughout the summer; flowering continuous during this period. Plants start flowering about six to seven weeks after planting rooted cuttings.

*Flower longevity.*—Flowers last about two weeks on the plant.

*Flower diameter.*—About 3 cm.

*Flower depth.*—About 2.5 cm.

*Flower buds.*—Length: About 8 mm. Diameter: About 5 mm. Shape: Globular. Color: 138A.

*Corolla.*—Shape/arrangement: Broadly tubular; five modified petals; upper two and lower three petals fused. Petal lobe apices: Rounded. Petal lobe margin: Entire. Petal lobe length: About 1 cm. Petal lobe width: About 7 mm. Texture, upper and lower surfaces of petal lobes: Smooth, glabrous; velvety. Color: When opening and fully opened, upper surface: 55A; throat, close to 5A with stripes, close to 59A. When opening and fully opened, lower surface: 55C.

*Calyx.*—Length: About 6 mm. Diameter: About 1 cm. Shape: Star-shaped. Sepal apex: Acute. Sepal margin: Entire. Sepal texture, upper and lower surfaces: Smooth, glabrous. Color, upper and lower surfaces: Close to 146A.

*Pedicels.*—Length: About 3 mm. Diameter: About 1 mm. Strength: Moderately strong; flexible. Angle: Erect to about 45° from the stem. Color: 138B.

*Reproductive organs.*—Androecium: Stamen quantity: Four per flower. Anther length: About 1 mm. Anther shape: Oval, bi-lobed. Anther color: 23A. Pollen amount: Moderate. Pollen color: Close to 23A. Gynoecium: Pistil quantity: One per flower. Pistil length: About 1.5 cm. Style length: About 1.3 cm. Style color: 54B. Stigma color: 138B. Ovary color: 145B.

*Seeds/fruits.*—Seed and fruit development has not been observed.

Disease/pest resistance: Plants of the new *Antirrhinum* have not been observed to be resistant to pathogens and pests common to *Antirrhinum.*

Temperature tolerance: Plants of the new *Antirrhinum* have been observed to tolerate temperatures from 0° C. to 32° C.

It is claimed:

1. A new and distinct cultivar of *Antirrhinum* plant named 'Amalia Pink', as illustrated and described.

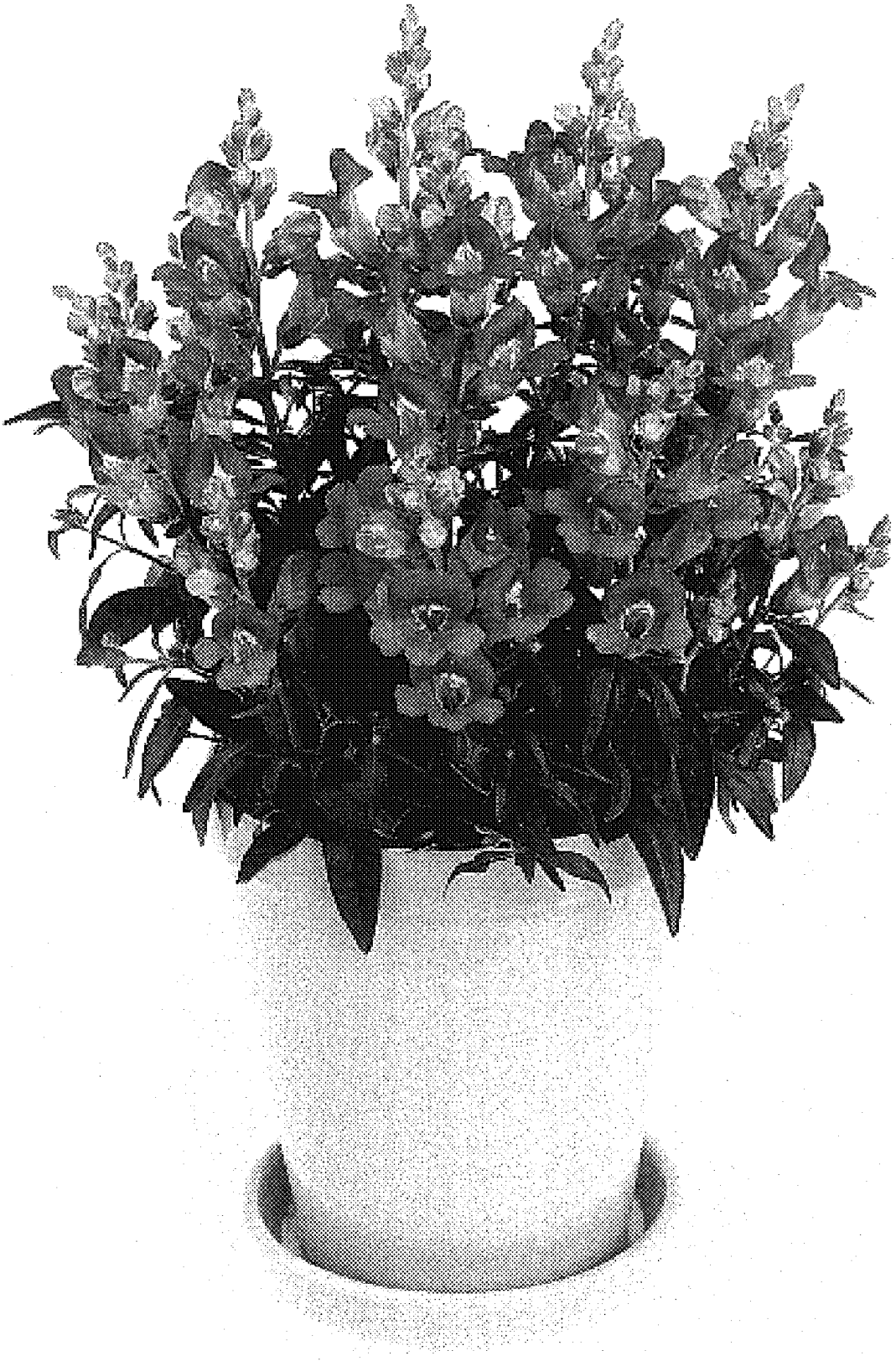

* * * * *